(12) United States Patent
Narula et al.

(10) Patent No.: US 7,375,062 B1
(45) Date of Patent: May 20, 2008

(54) SUBSTITUTED HYDROGENATED NAPHTHALENE DERIVATIVES AND THEIR USE IN FRAGRANCE FORMULATIONS

(75) Inventors: Anubhav P. S. Narula, Hazlet, NJ (US); Edward Mark Arruda, Easton, PA (US); Paul Pieschl, Sparta, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 11/556,801

(22) Filed: Nov. 6, 2006

(51) Int. Cl.
    *C11D 3/50* (2006.01)
(52) U.S. Cl. .................. 510/104; 568/819; 512/14
(58) Field of Classification Search ................ 510/104; 568/819; 512/14
    See application file for complete search history.

(56) References Cited

U.S. PATENT DOCUMENTS 5,084,440 A * 1/1992 Baudin et al. ............. 512/12
5,332,725 A * 7/1994 Baudin ..................... 512/14

FOREIGN PATENT DOCUMENTS

EP          595197       *  5/1994

\* cited by examiner

*Primary Examiner*—John R. Hardee
(74) *Attorney, Agent, or Firm*—Elizabeth M. Quirk; XuFan Tseng; Joseph F. Leightner

(57) ABSTRACT

The present invention is directed to novel compounds of the general formula

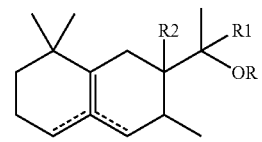

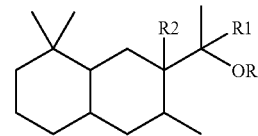

wherein R is selected from the group consisting of hydrogen, a straight, branched or cyclic alkyl that may or may not be unsaturated, alkenyl groups, an acetyl group, a substituted acetyl groups, an alkoxy ether group or alkyl substituted alkoxy ether moieties with each R, other than hydrogen comprising from 1 to 10 carbon atoms;

$R^1$, $R^2$ and $R^3$ independently represent hydrogen, a C1-C4 alkyl group such as methyl and ethyl and in which one of the dashed lines is a double bond and the other dashed line is a single bond.

14 Claims, No Drawings

SUBSTITUTED HYDROGENATED NAPHTHALENE DERIVATIVES AND THEIR USE IN FRAGRANCE FORMULATIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by Formula I and II set forth below:

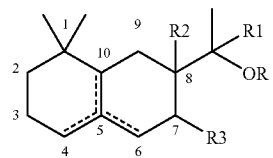

Formula I

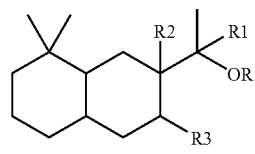

Formula II wherein R is hydrogen, a straight, branched or cyclic hydrocarbon moiety consisting of less than 10, most preferably less than 4 carbon atoms and containing single and/or double bonds, an acetyl group and substituted acetyl groups including cyclic groups, such as cyclopropyl acyl group, alkoxy ether groups and alkyl substituted alkoxy ether moieties such as, but not limited to, $CH_2$—O—$CH_2$—$R^5$ wherein $R^5$ is a C1-C4 alkyl group as well as double bond containing alkyl groups;

$R^1$, $R^2$ and $R^3$ may be independently selected from hydrogen, a C1-C4 alkyl group such as methyl and ethyl;

and when one of the dashed lines is a double bond and the other dashed line is a single bond.

Another embodiment of the invention is a method for enhancing a perfume composition by incorporating an olfactory acceptable amount of the compound provided above.

These and other embodiments of the present invention will be apparent by reading the following specification.

DETAILED DESCRIPTION OF THE INVENTION

R is selected from the group consisting of hydrogen, a straight, branched or cyclic alkyl that may or may not be unsaturated, alkenyl groups, an acetyl group, a substituted acetyl groups, an alkoxy ether group or alkyl substituted alkoxy ether moieties with each R, other than hydrogen comprising from 1 to 10 carbon atoms and more preferably 1 to 4 carbon atoms, alkoxy ether groups and alkyl substituted alkoxy ether moieties such as, but not limited to, $CH_2$—O—$CH_2$—$R^5$ wherein $R^5$ is a C1-C4 alkyl group as well as double bond containing alkyl groups;

$R^1$, $R^2$ and $R^3$ may be independently selected from hydrogen, a C1-C4 alkyl group such as methyl and ethyl; and in which one of the dashed lines is a double bond and the other dashed line is a single bond.

Suitable straight hydrocarbon moieties include alkanes such as but not limited to methyl, ethyl, propyl, butyl, pentyl, hexyl, and the like. Suitable branched hydrocarbon moieties include alkanes such as but not limited to isopropyl, sec-butyl, tert-butyl, diethyl, 2-ethyl-propyl, and the like. Suitable cyclic hydrocarbon moieties include cyclopropyl, cyclobutyl, cyclopentyl, cyclohexyl, phenyl, and the like. Suitable alkenes containing double bonds include ethene, propene, 1-butene, 2-butene, penta-1-3-deine, hepta-1,3,5-triene and the like.

In a preferred embodiment of the invention, the novel compounds of the present invention are represented by the following structures:

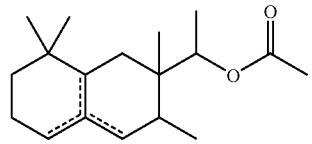

Structure I

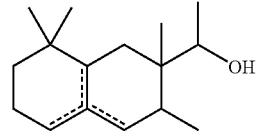

Structure II

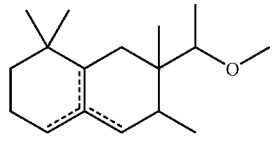

Structure III

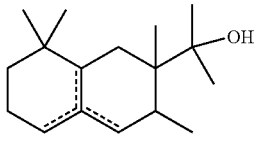

Structure IV

-continued

Structure V

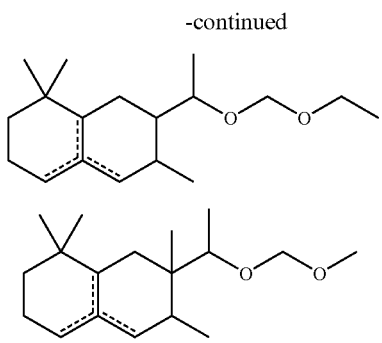

Structure VI

Structure VII

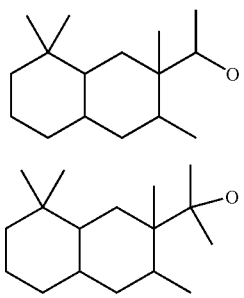

Structure VIII

Those with the skill in the art will appreciate that the following compounds:

Structure I is 2-Naphthalenemethanol,1,2,3,4,5,6,7,8-octahydro-alpha,2,3,8,8-pentamethyl-,acetate.

Structure II is 2-Naphthalenemethanol,1,2,3,4,5,6,7,8,-octahydro-alpha,2,3,8,8-pentamethyl.

Structure III is Naphthalenemethanol,1,2,3,4,5,6,7,8-octahydro-7-(1-methoxyethyl)-1,1,6,7-tetramethyl.

Structure IV is 2-Naphthalenemethanol,1,2,3,4,5,6,7,8-octahydro-alpha, alpha,2,3,8,8-hexamethyl.

Structure V is Naphthalene,7-[1-(ethoxymethoxy)ethyl]-1,2,3,4,5,6,7,8-octahydro-1,1,6-trimethyl.

Structure VI is Napthalene,1,2,3,4,5,6,7,8-octahydro-7-[1-(methoxymethoxy)ethyl]-1,1,6,7-tertramethyl-.

Structure VII 2-Naphthalenemethanol,1,2,3,4,5,6,7,8,9,10-decahydro-alpha,2,3,8,8-pentamethyl.

Structure VIII 2-Naphthalenemethanol,1,2,3,4,5,6,7,8,9,10-decahydro-alpha, alpha,2,3,8,8-hexamethyl.

The compounds of the present invention may be prepared from the corresponding myrcene and methyl pentenone via a Diels-Alder reaction followed by cyclization with an acid as delineated in the following sequence. Iso E super is a registered fragrance ingredient from International Flavors & Fragrances Inc.

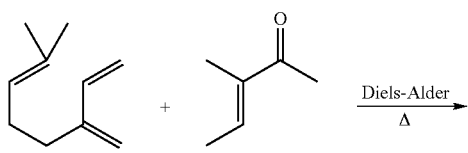

-continued

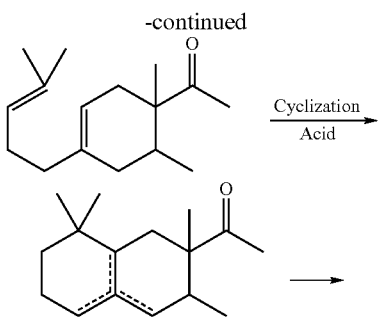

Cyclization
Acid

Various Derivatives cited in the Documents

The starting materials for the above reactions are available from the International Flavors & Fragrances Inc.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have discovered that the fragrance compounds of Structure I-VII impart naturalness to the fragrance formulations and are well suited for use as fragrance ingredients.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in Perfumes Cosmetics and Soaps, Second Edition, edited by W. A. Poucher, 1959. Among the fragrances provided in this treatise are acacia, cassie, chypre, cyclamen, fern, gardenia, hawthorn, heliotrope, honey-suckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following examples are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE A

Preparation of 2-Naphthalenemethanol,1,2,3,4,5,6,7, 8-octahydro-alpha,2,3,8,8-pentamethyl,acetate To a dry 2 L multi-neck round bottom flask fitted with an air stirrer, nitrogen inlet condenser and an addition funnel 452 g of Iso E Alcohol, 1000 ml of toluene and 15 g of pyridine were added and stirred. Then 400 g of acetic anhydride was added dropwise at a rate of 2 moles an hour. The mixture was aged for 2 hours and then quenched with 100 ml of cold water followed by 1 liter of 10% $Na_2CO_3$.

The product had woody, sweet, buttery and ionone fragrance notes.

The NMR spectrum of the 2-Naphthalenemethanol,1,2,3,4, 5,6,7,8-octahydro-alpha,2,3,8,8-pentamethyl,acetate is as follows: 0.7 ppm-1.0 ppm (m, 15H); 1.1 ppm-1.2 ppm (m, 5H); 1.3 ppm (m, 1H); 1.4 ppm (d, 3H); 1.5 ppm-2.0 ppm (m, 6H); 2.1 ppm (s, 3H); 4.9 ppm (m, 1H).

EXAMPLE B

Preparation of Naphthalene,1,2,3,4,5,6,7,8-octahydro-7-(1-methoxyethyl)-1,1,6,7-tetramethyl To a dry 2 L multi-neck round bottom flask fitted with an air stirrer, nitrogen inlet condenser and an addition funnel 22 g of NaH and 650 ml of THF (tetrahydrofuran) and heat to 60° C. Then add the 50 ml of THF with 120 g of Iso E Alcohol to the addition funnel dropwise. Then 78 g of $CH_3I$ was added dropwise and then cooled. The mixture was aged for 2 hours and then quenched with 100 ml of cold water followed by 1 liter of 10% $Na_2CO_3$.

The product had fatty, woody and ambery fragrance notes.

The NMR spectrum of the Naphthalene,1,2,3,4,5,6,7,8-octahydro-7-(1-methoxyethyl)-1,1,6,7-tetramethyl: 0.6 ppm (d, 2H); 0.7 ppm (s, H); 0.8 ppm (s, 3H); 0.9 ppm (s, 3H); 1.0 ppm (m, 4H); 1.1 ppm (m, 4H); 1.2 ppm (s, H); 1.5 ppm (m, 4H); 1.6 ppm (s, 3H); 2.1 ppm (s, H); 3.3 ppm (m, 3H).

EXAMPLE C

Preparation of 2-Naphthalenemethanol,1,2,3,4,5,6,7, 8-octahydro-alpha, alpha,2,3,8,8-hexamethyl To a dry 2 L multi-neck, 3 necked reaction flask equipped with a mechanical stirrer, nitrogen inlet addition funnel and a cooling bath, was charged methyl lithium (800 ml, 1.6 in ether) and cooled it to 0° C., Iso E Super (374 g) was added at 0° C. in 1 hour and aged the reaction for 1 hour. The reaction mixture was quenched with 10% acetic acid solution. Transferred the contents to a separating funnel, separated the aqueous layer and washed the organic layer with saturated sodium bicarbohydrate solution (1200 ml), concentrated the organic layer and washed it over to give 194 g of the product.

The product has a very nice ambery character, woody, vertofix, IsoE, musky and patchouli fragrance notes.

The NMR spectrum of the 2-Naphthalenemethanol,1,2,3,4, 5,6,7,8-octahydro-alpha, alpha,2,3,8,8-hexamethyl is as follows: 0.8 ppm (s, 3H); 0.9 ppm (s, 9H); 1.1 ppm (s, 3H); 1.2 ppm (s, 3H); 1.5-2.1 ppm (m, 10H); 4.8-5.25 ppm (m, 1H).

EXAMPLE D

Preparation of 2-Naphthalenemethanol,1,2,3,4,5,6, 78-octahydro-alpha,2,3,8,8-pentamethyl To a dry 2 L multi-neck, 3 necked reaction flask equipped with a mechanical stirrer, nitrogen inlet addition funnel and a cooling bath, was charged with NaBH4 and solvent at 30C and then Iso E Super was added and the temperature was increased to 45 C then cooled over the duration of the feed. The mixture was aged for 1 hour and then heated to reflux at 78 C and aged for 9 hours. Then 200 ml of IPA/$H_2O$ and heated to reflux at 85 C and aged for 15 hours and allow the mixtures to settle over two days. The layers were separated and washed with organic with brine (200 ml) settle and separate to give a 99% yield.

The product has fatty and woody fragrance notes.

The NMR spectrum of the 2-Naphthalenemethanol,1,2,3,4, 5,6,7,8-octahydro-alpha,2,3,8,8-pentamethyl is as follows: 0.65-0.9 ppm (ms, 12H); 1.1 ppm (d, 3H); 1.4-2.1 ppm (m, 7H); 3.75 ppm (m, 1H); 5.1-5.2 ppm (m, 1H).

EXAMPLE E

Preparation of Naphthalene,7-[1-(ethoxymethoxy) ethyl]-1,2,3,4,5,6,7,8-octahydro-1,1,6-trimethyl To a dry 2 L multi-neck, 3 necked reaction flask equipped with a mechanical stirrer, nitrogen inlet addition funnel and a cooling bath, was charged with alcohol, (ETO)2CH2, BF3OEt2 and CH3ONa and then heated to 80° C. The mixture was then distilled and then cooled and quenched with CH3ONa and washed base out with 100 ml water.

The product had woody, ionone, less ambery fragrance notes.

The NMR spectrum of the Naphthalene,7-[1-(ethoxymethoxy)ethyl]-1,2,3,4,5,6,7,8-octahydro-1,1,6-trimethyl is as follows: 0.6 ppm to 0.9 ppm (ms, 10H); 0.9 ppm (m, 4H); 1.0 ppm (s, 2H); 1.1 ppm-1.2 ppm (m, 6H); 1.3-1.5 ppm (m, 4H); 1.6 ppm (s, H); 1.7-1.9 (m, 3H); 2.1 ppm (s, H); 3.5 ppm-3.7 ppm (bs, 3H); 4.6 ppm (d, H); 4.8 ppm (d, H).

EXAMPLE F

Preparation of Napthalene 1,2,3,4,5,6,7,8-octahydro-7-[1-(methoxymethoxy)ethyl]-1,1,6,7-tertramethyl- To a dry 2 L multi-neck, 3 necked reaction flask equipped with a mechanical stirrer, nitrogen inlet addition funnel and a cooling bath, was charged with 236 g of Iso E Alcohol, 456 g of dimethoxy methane and 7.1 g of BF3OEt2. The mixture was then distilled and then cooled and quenched with CH3ONa and washed base out with 100 ml water.

The product had sweet, woody, buttery and grisalva fragrance notes.

The NMR spectrum of the Naphthalene,7-[1-(ethoxymethoxy)ethyl]-1,2,3,4,5,6,7,8-octahydro-1,1,6-trimethyl is as follows: 0.7 ppm-0.9 ppm (ms, 10H); 1.0 ppm (m, 4H); 1.1 ppm-1.2 ppm (m, 5H); 1.3 ppm-1.4 ppm (m, 4H); 1.5-1.7 ppm (m, 6H); 1.8 ppm-1.9 ppm (m, 3H); 2.1 ppm (s, H); 3.4 ppm (s, 3H); 3.6 ppm (s, H); 4.6 ppm (d, H); 4.8 ppm (d, H).

What is claimed is:

1. A compound of formula

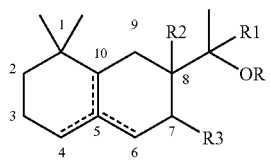

wherein R is selected from the group consisting of hydrogen, a straight, branched or cyclic alkyl that may or may not be unsaturated, alkenyl groups, an acetyl group, a substituted acetyl groups, an alkoxy ether group or alkyl substituted alkoxy ether moieties with each R, other than hydrogen comprising from 1 to 10 carbon atoms;

$R^1$ is selected from the group consisting of hydrogen or a C1-C4 alkyl group and $R^2$ and $R^3$ is independently equal to methyl;

and wherein one of the dashed lines between the 5 and 10 position, the 4 and 5 position and the 5 and 6 position represents a second C—C bond in a C=C double bond.

2. A compound of claim 1, wherein R is an acetyl group, $R^1$ is hydrogen and $R^2$ and $R^3$ independently represent methyl.

3. A compound of claim 1, wherein R and $R^1$ independently represent hydrogen and $R^2$ and $R^3$ independently represent methyl.

4. A compound of claim 1, wherein $R^1$ is hydrogen and R, $R^2$ and $R^3$ independently represent methyl.

5. A compound of claim 1, wherein R is H and $R^1$, $R^2$ and $R^3$ independently represent methyl.

6. A compound of claim 1, wherein R is an alkyl substituted alkoxy ether moiety selected from $CH^2$—O—$CH_2$—$R^5$ wherein $R^5$ is a C1-C4 alkyl group and $R^1$ represents hydrogen and $R^2$ and $R^3$ independently equal methyl.

7. A fragrance formulation containing an olfactory effective amount of the compound of claim 1.

8. A fragrance product containing a compound of claim 1.

9. A method of improving, enhancing or modifying a fragrance formulation through the addition of an olfactory acceptable amount of the compound of claim 1.

10. The method of claim 9 wherein the fragrance formulation is incorporated into a product selected from perfumes, colognes, toilet waters, cosmetic products, personal care products, fabric care products, cleaning products and air fresheners.

11. The method of claim 10 wherein the cleaning product is selected from the group consisting of detergents, dishwashing compositions, scrubbing compounds and window cleaners.

12. The method of claim 11, wherein the amount incorporated into a fragrance is from about 0.005 to about 10 weight percent.

13. The method of claim 11, wherein the amount incorporated into a fragrance is from about 0.5 to about 8 weight percent.

14. The method of claim 11, wherein the amount of incorporated into a fragrance is from about 1 to about 7 weight percent.

* * * * *